United States Patent [19]

Tse

[11] 4,255,606
[45] Mar. 10, 1981

[54] IMPROVED PARA- AND ORTHO-XYLENE ISOMERIZATION BY ADDING PENTANE

[75] Inventor: Harold F. Tse, Kearny, N.J.

[73] Assignee: Engelhard Minerals & Chemicals Corporation, Iselin, N.J.

[21] Appl. No.: 98,099

[22] Filed: Nov. 28, 1979

[51] Int. Cl.$^3$ ................................................. C07F 5/22
[52] U.S. Cl. ................................... 585/482; 585/477
[58] Field of Search ........................ 585/481, 482, 477

[56] References Cited

U.S. PATENT DOCUMENTS

| | | | |
|---|---|---|---|
| 3,538,173 | 11/1970 | Berger et al. | 585/482 |
| 3,553,276 | 1/1971 | Berger et al. | 585/482 |
| 4,128,591 | 12/1978 | Carr et al. | 585/481 |

Primary Examiner—Veronica O'Keefe

[57] ABSTRACT

An isomerization process for the production of desired isomers of aromatic hydrocarbons containing eight carbon atoms per molecule, i.e., para-xylene and ortho-xylene, from a mixture of aromatic hydrocarbons containing eight carbon atoms per molecule wherein yields of the desired carbon, are increased by incorporating an aliphatic hydrocarbon, e.g., n-pentane, in the feedstock for the process.

14 Claims, No Drawings

IMPROVED PARA- AND ORTHO-XYLENE ISOMERIZATION BY ADDING PENTANE

The present invention relates to a process for the isomerization of eight carbon atom aromatic hydrocarbons. In one of its more specific aspects, this invention relates to an improved aromatic isomerization process wherein the yields of desired ortho- and para-xylenes are maximized by incorporation into the feed stream to the isomerization process a minor but significant amount of an aliphatic hydrocarbon, especially those containing from five to seven carbon atoms per molecule, for example, normal pentane. In another specific aspect, the process of this invention comprises the recycle of hydrocarbons containing five to seven carbon atoms per molecule and/or precursors of such hydrocarbons which are inherently produced as a byproduct in the isomerization process, to reduce the loss of the desired xylene isomers by undesirable side reactions.

The production of para- and ortho-xylenes by isomerization of aromatic hydrocarbons containing eight carbon atoms per molecule is well known, and is described, for example, in U.S. Pat. Nos. 3,538,173; 3,553,276; and 4,128,591. In the known isomerization process, a nonequilibrium feedstock, lean (relative to the equilibrium mixture) in xylenes and rich in ethylbenzene, obtained as described below, is contacted at elevated temperature and pressure with a suitable catalyst, usually a platinum or palladium catalyst, to drive the mixture toward the equilibrium composition of $C_8$ aromatics. The objective is to enhance the yield of ortho- and para-xylenes, which are removed from the product of the $C_8$ isomerization process. The residual material from which the xylenes have been recovered, is recycled, together with fresh feed, to the $C_8$ isomerization reactor.

The liquid product obtained from the $C_8$ isomerization reactor is conventionally sent to distillation towers in order to remove $C_4$ and lighter compounds (light ends) which are usually utilized as fuel and may be employed in a furnace used to heat the feed prior to introducing it into the $C_8$ isomerization reactor.

The $C_5$–$C_7$ side stream and the $C_9+$ heavy ends obtained from the distillation operation are, in the prior, art, usually sent to a gasoline blending operation for utilization as a component of the gasoline. In accordance with the present invention, as described more fully below, this predominantly $C_5$–$C_7$ side stream (or any other suitable source of $C_5$–$C_7$ hydrocarbons or their precursors) is recycled to the $C_8$ isomerization process.

The feed stock for the $C_8$ isomerization process usually is obtained from catalytic or pyrolytic conversions of hydrocarbon distillates by hydrocracking catalytic reforming, thermal cracking or related processes and is usually a fraction having a boiling range within the range from about 120° C. to about 145° C.

A typical feedstream for the $C_8$ isomerization process is prepared by solvent extraction and/or distillation and contains essentially only $C_8$ aromatics, that is, the three xylenes (para, meta, and ortho) and about 15–65 weight percent of ethylbenzene. Since ethylbenzene will be in the range of only about 7–10 weight percent equilibrium mixtures, it must be isomerized to xylenes or destroyed. In the process of the present invention a portion of the ethylbenzene is converted to xylenes.

During the course of the isomerization reaction, some of the $C_8$ aromatic hydrocarbon content is lost due to side reactions which form other hydrocarbons, such as toluene, benzene, and $C_1$ to $C_9$ aliphatic and aromatic hydrocarbons. It has been proposed, in U.S. Pat. No. 3,553,276, to increase the concentration of toluene in the feed to a $C_8$ aromatic isomerization process to at least two times its normal value to lower naphthene losses while in the process of U.S. Pat. No. 3,538,173, the concentration of $C_8$ naphthenes to the reactor is maintained within a certain range relative to the $C_8$ aromatic charge to improve the yield of the desired xylene isomers.

The stated purpose of the recycle of toluene to the feed stream by the process of U.S. Pat. No. 3,553,276 is to reduce the loss of naphthenes, which, because of their relative volatilities, are difficult to separate from toluene; toluene is a by-product of the reaction which ultimately must be removed from the recycle stream. In this prior art process, the toluene concentration is permitted to build up in the recycle stream in order to reduce losses of naphthenes with the toluene separated from the recycle stream.

The stated purpose of recycling naphthenes in U.S. Pat. No. 3,538,173 is to maintain a $C_8$ naphthene content in the $C_8$ aromatic charge to the isomerization reaction zone within the range of 2 to 9% by weight of the $C_8$ aromatics in the charge. It is stated that these concentrations of $C_8$ naphthenes insure conversion of ethylbenzene to xylenes.

In accordance with the present invention, there is provided, in a process for the isomerization of aromatic hydrocarbons containing eight carbon atoms per molecule to produce para-xylene and ortho-xylene, and in which the aromatic hydrocarbons are contacted in an isomerization zone with an isomerization catalyst at elevated temperature and pressure suitable for such isomerization, in the presence of added hydrogen, and the contacted product withdrawn from the zone, the improvement which comprises introducing into the isomerization zone from 1 to 10 weight percent, based on the weight of the total feed introduced into the zone, of at least one aliphatic hydrocarbon containing at least 5 carbon atoms per molecule. At least a part of the aliphatic hydrocarbon may be introduced into the zone by separation from the contacted material withdrawn from the zone a recycle stream predominantly composed of the aliphatic hydrocarbon. Generally, in one aspect of the present invention an aliphatic hydrocarbon is included in the feed to a $C_8$ aromatic isomerization process to improve the yields of the desired xylene isomers. It has been found, unexpectedly, that the addition of an aliphatic hydrocarbon such as n-pentane to the feed stream, either with or without the addition of toluene, increases the $C_8$ ring retention and reduces the yields of undesirable by-product hydrocarbons, including gaseous hydrocarbons containing 1 to 4 carbon atoms per molecule, i.e., the $C_1$–$C_4$ aliphatic hydrocarbons. In one embodiment of this invention, n-pentane is included in the $C_8$ aromatic charge to the isomerization zone in an amount within the range of from about 1 to 10, preferably from about 2 to about 6 weight percent of the total weight of the charge. In another specific embodiment of the invention, both n-pentane in the range of about 1 to 10 weight percent, preferably from about 2 to about 6 weight percent, based on the total weight of charge, and toluene in an amount within the range of 1 to 10 weight percent based on the total weight of charge, are included in the charge to the isomerization reaction zone. In still another embodiment of the invention, a mixture of $C_5$–$C_7$ hydrocarbons in an amount within the range of from about 2 to about 6 weight percent is recycled to the isomerization reactor from the effluent stream withdrawn therefrom. It is also within the scope of this invention to incorporate a n-pentane precursor, such as nonane, into the charge to the isomerization reaction zone. Generally, recycled streams, whether $C_5$–$C_7$ or n-pentane will also contain a small quantity of higher molecular weight hydrocarbons such as $C_9$ hydrocarbons, so that in practice, a recycled $C_5$–$C_7$ stream is, more precisely, a recycled predominantly $C_5$–$C_7$ stream. It will be understood that in commercial practice there is normally minor quantities of materials outside the specified range of a stream, these materials being present in a commercially and technically insignificant amount. A suitable quantity of hydrogen is, of course, also charged to the isomerization reaction zone.

No simple reaction mechanism can explain the reduction in side reactions and increase in $C_8$ ring retention which results when a low molecular weight aliphatic hydrocarbon, n-pentane for example, is added to the charge to the isomerization reactor since no reversible equilibrium reactions are possible. In fact, it is surprising that the inclusion of a $C_5$ to $C_7$ hydrocarbon component, e.g., pentane, would increase the desired $C_8$ ring formation since $C_5$ to $C_7$ components do not have enough carbon atoms to form an eight carbon atom ring. While not intending to be bound thereby, one theory which may explain this phenomenon is that the $C_5$ to $C_7$ components added in accordance with this invention may have a tendency to occupy cracking sites on the catalysts and therefore reduce opportunities for the catalyst to crack $C_8$ rings. Generally, the desired lower limit of 1% of the total feed comprising the $C_5$–$C_7$ hydrocarbon or its precursor, is set by the minimum quantity of such material hydrocarbon which has a noticeable or significant beneficial effect on the process.

In the process of the present invention, the $C_8$ ring loss is reduced and yields of desired products increased by the inclusion of $C_5$ to $C_7$ aliphatic hydrocarbons in the feed to the isomerization process, with or without the addition of toluene. The addition of normal pentane to the isomerization feed stream in amounts ranging from about 2 to 6 weight percent of the $C_8$ aromatics in the feed stream has been found to be particularly effective for improving $C_8$ ring retention and conversion of the $C_8$ hydrocarbons to the desired xylene isomers. As there is no equilibrium relationship between the lower molecular weight hydrocarbons and the xylenes, the effectiveness of these materials in the feed stream for suppression of losses and improved conversion cannot be explained by the laws of mass action.

In processes for the production of xylenes, the ortho- and para-xylenes are the preferred products. Para-xylene is principally used in the preparation of polyesters while ortho-xylene is used principally in preparation of phthalic anhydride. Meta-xylene has fewer important end uses and thus it is usually converted to the para-form, which has greater commercial value. Isomerization of the mixed isomers is carried out at an elevated temperature in the presence of a catalyst comprising a noble metal on an acid support, such as silica-alumina, in the presence of hydrogen. These reaction conditions favor the formation of an equilibrium mixture of the xylenes from a feedstock which is not at equilibrium, being lean in the desired ortho- and para-xylenes. The desired ortho- and para-xylene isomers are separated from the reaction product of the isomerization reaction process and the unconverted isomers recycled to the process for further conversion. The undesired isomers, for example, meta-xylene and ethylbenzene, are ultimately recycled to extinction.

The catalyst employed in the process of the present invention preferably comprises platinum or palladium on a high surface area alumina support. The alumina support is preferably a high surface area alumina in the form of extrudates or spheres ranging in size from about 1 to 10 mm in diameter and having deposited thereon from about 0.1 to about 0.5% by weight platinum or palladium, based on the weight of the alumina substrate. A preferred catalyst is that disclosed in U.S. Pat. No. 4,128,591, the disclosure of which is incorporated herein by reference, which consists essentially of extrudates comprising a catalytically active amount of platinum alone or in combination with one or more of the elements palladium, ruthenium, rhodium, iridium, and rhenium, deposited on particulate alumina and then admixed with particulate hydrogen mordenite containing less than 0.1 gram equivalent of alkali and alkaline earth metal cations per gram atom of aluminum and having a silica to alumina ratio greater than about 9–11 to 1 and less than about 17 to 1, preferably 14 to 1. The mixture may be formed into extrudates by wetting with water either before or after mixing the particulate components, dried, and calcined at 500° C. for 2 hours.

Excellent results have been obtained by the process of this invention by (a) the inclusion of from 2 to 6 weight percent n-pentane in the feed stream to the reactor, (b) by recycle of $C_5$–$C_7$ hydrocarbons to the process in an amount within the range of 2 to 6 weight percent of the total feed, and (c) by the addition of a mixture of toluene and n-pentane to the feed in an amount ranging from 2 to 6 weight percent toluene and 2 to 6 weight percent n-pentane. The effectiveness of the process of the present invention for improving the yields of ortho- and para-xylenes from mixed $C_8$ aromatics is illustrated in the following examples. The runs of Examples 1–11 were carried out in a single tube 1 inch diameter reactor in which was disposed a catalyst as described in the examples.

EXAMPLES 1–4

Examples 1 to 4 illustrate the effect of n-pentane addition of $C_8$ aromatics feedstock. The following runs were made at 13 atm (175 psig) with a feed supplying hydrogen and hydrocarbons in a hydrogen to hydrocarbon mole ratio of 8:1 and at a weight hourly space velocity (unit weight of feed/hr/per unit weight of catalyst) of 3.6 at two different temperature levels—430° C. (800° F.) and 440° C. (825° F.)—both with and without the addition of n-pentane to the feed to the isomerization reactor. The runs were carried out in the presence of a catalyst comprising 0.4 weight percent platinum on a support comprising 50 weight percent hydrogen mordenite and 50 weight percent gamma alumina substrate in the form of cylindrical extrudates 1/16 inch in diameter and 0.3 inch in length.

EXAMPLES 1 AND 2

Isomerization without n-pentane

In these examples, no n-pentane was included in the feed to the reactor.

| | Weight % Components In: | | |
|---|---|---|---|
| | | Products* | |
| Components | Feed | Example 1 430° C. | Example 2 440° C. |
| $C_1$-$C_4$ Hydrocarbons | — | 1.1 | 1.5 |
| i-Pentane | — | 0.3 | 0.3 |
| n-Pentane | — | 0.1 | 0.2 |
| Benzene | 0.1 | 0.4 | 0.7 |
| Toluenes | 0.3 | 1.5 | 2.1 |
| o-Xylene | 19.9 | 19.3 | 19.3 |
| m-Xylene | 55.8 | 42.8 | 42.4 |
| p-Xylene | 7.9 | 18.8 | 18.9 |
| Ethylbenzene | 15.5 | 11.1 | 10.9 |
| $C_6$ Naphthenes | — | 0.1 | 0.1 |
| $C_7$ Naphthenes | — | 0.1 | 0.1 |
| $C_8$ Paraffins | — | 0.2 | 0.1 |
| $C_8$ Naphthenes | 0.4 | 3.5 | 1.7 |
| $C_9$+ Aromatics | 0.1 | 1.6 | 2.4 |

*Product compositions are expressed in weight percent of product based on the $C_8$ aromatics (xylenes and ethylbenzene) in the feed, ignoring other feed components and added hydrogen.

EXAMPLES 3 AND 4

Effects of n-pentane

In these examples, n-pentane in an amount equal to approximately 4 weight percent, based on the weight of the aromatics, was included in the feedstream to the reactor.

| | Weight % Components In: | | |
|---|---|---|---|
| | | Products* | |
| Component | Feed | Example 3 430° C. | Example 4 440° C. |
| $C_1$-$C_4$ Hydrocarbons | — | 0.9 | 1.2 |
| Iso-pentane | — | 0.8 | 1.2 |
| n-Pentane | 4.2 | 2.4 | 2.3 |
| Benzene | — | 0.4 | 0.7 |
| Toluene | 0.1 | 1.5 | 2.2 |
| o-Xylene | 19.1 | 19.6 | 19.4 |
| m-Xylene | 53.4 | 44.2 | 43.4 |
| p-Xylene | 7.6 | 19.0 | 19.1 |
| Ethylbenzene | 14.9 | 11.2 | 11.0 |
| $C_6$ Naphthenes | — | 0.1 | 0.1 |
| $C_7$ Naphthenes | — | 0.1 | 0.1 |
| $C_8$ Paraffins | — | 0.2 | 0.1 |
| $C_8$ Naphthenes | 0.3 | 3.2 | 1.8 |
| $C_9$+ Aromatics | 0.4 | 1.8 | 2.5 |

*Product compositions are expressed in weight percent of product base on $C_8$ aromatics (xylenes and ethylbenzene) in the feed, ignoring other feed components and added hydrogen.

It will be evident from Examples 1–4 that the inclusion of n-pentane in the feed to the isomerization reactor increases the yield of $C_8$ aromatics in the product, i.e., improves product selectivity, at both temperature levels. The results of Examples 1–4 are summarized below in terms of $C_8$ aromatics and $C_8$ rings ($C_8$ aromatic and $C_8$ naphthene) in the products at the two temperatures:

| Weight % in Product | Without n-Pentane Added | | With n-Pentane Added | | Absolute Difference | |
|---|---|---|---|---|---|---|
| | 430° C. | 440° C. | 430° C. | 440° C. | 430° C. | 440° C. |
| $C_8$ Aromatics | 92.0 | 91.5 | 94.0 | 92.9 | +2.0 | +1.4 |
| $C_8$ Rings | 95.5 | 93.2 | 97.2 | 94.7 | +1.7 | +1.5 |

EXAMPLES 5–7

Effects of toluene and n-pentane plus toluene

Tests were made to determine the relative effects of toluene alone and n-pentane in addition to toluene on the $C_8$ aromatics yield and $C_8$ ring retention in an aromatics isomerization reaction employing a catalyst comprising 0.48 weight percent platinum on a support comprising 15 weight percent hydrogen mordenite and 85 weight percent gamma alumina in the form of cylindrical extrudates 1/16 inch in diameter and 0.3 inch in length. These runs were carried out at a reaction temperature of 413° C. (775° F.) and a pressure of 13 atm (175 psig) with a hydrogen to hydrocarbon mole ratio of 8:1 at a weight hourly space velocity (unit weight of feed/hr/unit weight of catalyst) of 3.6.

In Example 5, a straight aromatics feedstock is fed to the isomerization reactor. In Example 6, toluene is added to the aromatics feedstock, and in Example 7, both n-pentane (2.4 weight percent) and toluene are added to the aromatics feedstream. The results are shown below wherein all compositions are expressed as percentages by weight.

| | Example 5 | | Example 6 | | Example 7 | |
|---|---|---|---|---|---|---|
| Component | Feed | Product* | Feed | Product* | Feed | Product* |
| n-Pentane | — | 0.2 | — | 0.2 | 2.4 | 1.2 |
| i-Pentane | — | 0.5 | — | 0.6 | — | 0.7 |
| $C_8$ Naphthenes | 0.1 | 6.6 | 0.4 | 7.1 | 0.4 | 7.7 |
| $C_7$ Naphthenes | — | 0.3 | — | 0.6 | — | 0.8 |
| Benzene | — | 0.2 | — | 0.2 | — | 0.2 |
| Toluene | 0.3 | 1.2 | 4.9 | 5.0 | 5.2 | 5.2 |
| Ethylbenzene | 15.7 | 11.1 | 15.0 | 11.1 | 14.6 | 11.3 |
| p-Xylene | 8.0 | 17.7 | 7.8 | 17.8 | 7.5 | 17.8 |
| m-Xylene | 56.0 | 42.3 | 52.7 | 42.6 | 51.2 | 43.5 |
| o-Xylene | 19.9 | 18.9 | 19.1 | 19.0 | 18.6 | 19.3 |
| $C_9$+ Aromatics | — | 1.1 | 0.1 | 1.1 | 0.1 | 1.0 |
| $C_8$ Aromatics Yield | | 89.9** | | 90.5** | | 91.9** |
| Ring Retention ($C_8$) | | 96.1 ** | | 97.1** | | 99.0** |

*Product compositions are expressed in weight percent of product based on the $C_8$ aromatics (xylenes and ethylbenzene) in the feed, ignoring other feed components and added hydrogen.
**Expressed as weight percent of the corresponding component in the feed. $C_8$ rings in the feed are calculated based upon xylenes, ethyl benzene and $C_8$ naphthenes in the feed.

EXAMPLES 8 AND 9

Effect of n-pentane (2.0 Wt. %)

In a test similar to those of Examples 6 and 7, n-pentane alone in an amount equivalent to 2.0 weight percent of the feed is added to the aromatics feedstock of Example 5 and passed at a weight hourly space velocity (unit weight of feed/hr/unit weight of catalyst) of 3.6 at 413° C. (775° F.), a pressure of 13 atm (175 psig), and a hydrogen to hydrocarbon ratio of 8:1 into contact with a catalyst comprising 0.4 weight percent platinum on a support comprising 50 weight percent hydrogen mordenite and 50 weight percent gamma alumina, in the form of cylindrical extrudates 1/16 inch in diameter and 0.3 inch in length.

In Example 8, straight aromatics feedstock is supplied to the isomerization reaction whereas in Example 9, 2.2 weight percent n-pentane is included in the feed to the isomerization reactor. In the following tables, all compositions are expressed as percentages by weight.

| | Example 8 | | Example 9 | |
|---|---|---|---|---|
| Component | Feed | Product* | Feed | Product* |
| i-Pentane | — | 0.3 | — | 0.5 |
| n-Pentane | — | 0.1 | 2.2 | 1.2 |
| $C_8$ Naphthenes | 0.1 | 7.5 | 0.4 | 7.0 |
| $C_7$ Naphthenes | — | 0.3 | — | 0.3 |
| Benzene | — | 0.2 | — | 0.2 |
| Toluene | 0.3 | 0.9 | 0.3 | 0.9 |
| Ethylbenzene | 15.8 | 10.3 | 15.4 | 10.3 |
| p-Xylene | 8.1 | 18.0 | 8.1 | 18.3 |
| m-Xylene | 55.7 | 42.3 | 53.8 | 43.8 |
| o-Xylene | 20.0 | 19.1 | 19.7 | 19.2 |
| $C_9+$ Aromatics | — | 1.0 | 0.1 | 1.0 |
| $C_8$ Aromatics Yield | | 89.6** | | 91.5* |
| Ring Retention ($C_8$) | | 96.9** | | 98.1* |

*Product compositions are expressed in weight percent of product based on the $C_8$ aromatics (xylenes and ethylbenzene) in the feed, ignoring other feed components and added hydrogen.
**Expressed as weight percent of the corresponding component in the feed. $C_8$ rings in the feed are calculated based upon xylenes, ethyl benzene and $C_8$ naphthenes in the feed.

It will be seen that the increased yields of $C_8$ aromatics and increased rate of $C_8$ ring retention obtainable by the addition of n-pentane alone is superior to those obtainable by the addition of toluene alone and that obtained by the addition of n-pentane plus toluene is superior to that obtained by the addition of toluene alone. The results of Examples 5–9 are summarized in the following table; the numbers express percent by weight in the product of the quantity of, respectively, $C_8$ aromatics and $C_8$ rings present in the feed.

| | Yields | |
|---|---|---|
| Additive | $C_8$ Aromatics | $C_8$ Rings |
| None | 89.9 (89.6) | 96.1 (96.9) |
| Toluene (4.6%) | 90.5 | 97.1 |
| n-Pentane (2.0%) | 91.5 | 98.1 |
| Toluene (4.9%) + n-Pentane (2.2%) | 91.9 | 99.0 |

EXAMPLES 10 AND 11

In a set of tests conducted under the reaction conditions and with the same catalyst composition as Examples 8 and 9; 2,2,5-trimethyl hexane was added to the feed to an aromatics isomerization unit to test the effectiveness of n-pentane precursors, such as $C_9$ alkanes, in the process of this invention. In Example 10, a straight aromatics feedstock is fed to the isomerization reactor whereas in Example 11, 3.9 weight percent of the $C_9$ isoparaffin is added to the feedstream. Results are shown in the following table wherein all compositions are expressed as percentages by weight and product compositions are reported on the basis of the $C_8$ aromatics content of the feed to the isomerization reactor.

| | Example 10 | | Example 11 | |
|---|---|---|---|---|
| Component | Feed | Product* | Feed | Product* |
| $C_1$–$C_4$ Hydrocarbon | — | 1.5 | — | 1.7 |
| i-Pentane | — | 0.3 | — | 1.9 |
| n-Pentane | — | 0.2 | — | 0.7 |
| $C_9$ Paraffins | — | — | 3.6 | — |
| $C_6$–$C_7$ Naphthenes | — | 0.2 | 0.4 | 0.2 |
| $C_8$ Naphthenes | 0.4 | 0.1 | 0.1 | — |
| Benzene | 0.1 | 0.7 | — | 0.5 |
| Toluene | 0.3 | 2.1 | 0.3 | 2.0 |
| Ethylbenzene | 15.5 | 10.9 | 15.2 | 10.9 |
| p-Xylene | 7.9 | 18.9 | 7.7 | 19.0 |
| m-Xylene | 55.8 | 42.4 | 53.2 | 43.3 |
| o-Xylene | 19.9 | 19.3 | 19.4 | 19.5 |
| $C_9+$ Aromatics | 0.1 | 2.4 | 0.1 | 2.8 |
| Total Aromatics | | 96.7** | | 98.1* |
| $C_8$ Aromatic Yield | | 91.5** | | 92.8* |
| $C_8$ Ring Retention | | 92.8** | | 94.8* |

*Product compositions are expressed in weight percent or product based on the $C_8$ aromatics (xylenes and ethylbenzenes) in the feed, ignoring other feed components and added hydrogen.
**Expressed as weight percent of the corresponding component in the feed. $C_8$ rings in the feed are based upon xylenes, ethyl benzene and $C_8$ naphthenes in the feed.

EXAMPLES 12 AND 13

Effect of Increasing Light Hydrocarbon Content of Feed In a Commercial Plant Test runs were conducted in the isomerization reactor of a commercial refinery. In one case (Example 12), a fresh feed containing about 3 wt. % light hydrocarbons was introduced into the reactor. In another case (Example 13) the total light hydrocarbon content in the feed was increased to about 5.3 wt. % by recycle of a light hydrocarbon fraction from the process. In Example 12, there was introduced into the isomerization reactor of a commercial refinery 55,943 kg/hr of feed at a weight hourly space velocity of 1.6. The reactor contained 33,800 kilograms of a catalyst comprised of 0.4% platinum on a support of 70 wt. % eta alumina and 30 wt. % of a silica-alumina acidic function. The total feed of 55,943 kg/hr included 17,670 kg/hr of fresh feed and 38,273 kg/hr of liquor obtained from the crystallizer utilized to separate para-xylene from the effluent of the isomerization reactor. The fresh feed in this run contained 1,679 kg/hr of a $C_5$–$C_7$ hydrocarbon material, the latter thus comprising about 3 wt. % of the total feed to the isomerization reactor. In Example 13, the same conditions were run in the same equipment, except that 1,995 kg/hr of a $C_5$–$C_7$ hydrocarbon recycle from the operation was introduced into the feed together with 1,020 kg/hr of $C_5$–$C_7$ hydrocarbons introduced with the fresh feed. Accordingly, in Example 13, the total $C_5$–$C_7$ hydrocarbon in the combined feed was 3,015 kg/hr or 5.3 wt. % of the total combined feed. As will be noted from the following data, the increase in $C_5$–$C_7$ hydrocarbons provided by the recycled material added to the isomerization reactor showed a marked improvement in the approaches to equilibrium of the xylenes, and an increase of 2% in overall $C_8$ ring retention.

| Effects of Recycle of $C_5$–$C_7$ FRACTION | | |
|---|---|---|
| | Example 12 | Example 13 |
| Isomerizer Feed (Total, Kg/hr) | 55,943 | 55,279 |
| Fresh Feed, Kg/hr | 17,670 | 17,011 |
| Crystallizer Effluent, Kg/hr | 38,273 | 40,278 |
| $C_5$–$C_7$ Hydrocarbons introduced in fresh feed; Kg/hr | 1,679 | 1,020 |
| $C_5$–$C_7$ Hydrocarbons Recycled, Kg/hr | None | 1,995 |
| Percentage $C_5$–$C_7$ hydrocarbons in Isomerizer feed | 3.0 | 5.3 |
| Approaches to Equilibrium, %: | | |
| Meta-xylene | 83 | 102 |
| Para-xylene | 88 | 102 |
| Ortho-xylene | 77 | 102 |
| Ethyl-benzene | 49 | 44 |
| Ethyl-Benzene Conversion | 30 | 26 |
| $C_8$ Ring Retention, % | 95 | 97 |

The foregoing examples illustrate the beneficial results in aromatics isomerization which may be obtained by incorporating aliphatic hydrocarbons in the feed to the process in accordance with this invention.

I claim:

1. In a process for the isomerization of aromatic hydrocarbons containing eight carbon atoms per molecule to produce para-xylene and ortho-xylene wherein said aromatic hydrocarbons are contacted in an isomerization zone with an isomerization catalyst at elevated temperature and pressure suitable for such isomerization in the presence of added hydrogen and the contacted material withdrawn from said zone, the improvement which comprises introducing into said isomerization zone from about 1 to 10 weight percent of the total feed to the isomerization zone, of at least one aliphatic hydrocarbon containing at least 5 carbon atoms per molecule.

2. A process according to claim 1 wherein at least a part of said aliphatic hydrocarbon is introduced into said zone by separating from the contacted material withdrawn from said zone a recycle stream predominantly composed of said aliphatic hydrocarbon and returning said recycle stream to said zone.

3. A process according to claim 1 or claim 2 wherein said aliphatic hydrocarbon has from 5 to 7 carbon atoms per molecule.

4. A process according to claim 3 wherein said aliphatic hydrocarbon is n-pentane.

5. A process according to claim 1 or claim 2 wherein at least a portion of said aliphatic hydrocarbon is a precursor of n-pentane said precursor yielding n-pentane under the conditions of said isomerization zone.

6. A process according to claim 1 or claim 2 wherein said catalyst comprises a noble metal supported on a silica-alumina base.

7. A process according to claim 6 in which said silica-alumina base comprises alumina admixed with a zeolite.

8. A process according to claim 1 or claim 2 wherein said catalyst comprises a noble metal on a support comprising a mixture of gamma alumina and hydrogen mordenite.

9. A process according to claim 1 or claim 2 wherein said catalyst comprises platinum supported on a silica-alumina base.

10. A process according to claim 1 or claim 2 wherein said catalyst comprises 0.1 to 0.5 weight percent platinum on a base comprising 15 to 50 weight percent hydrogen mordenite and 50 to 85 weight percent gamma alumina.

11. A process according to claim 1 or claim 2 wherein said low molecular weight hydrocarbon comprises a mixture of $C_5$ to $C_7$ hydrocarbons.

12. A process according to claim 1 or claim 2 wherein said aliphatic hydrocarbon introduced into said isomerization zone is from about 2 to 6 weight % of the total feed.

13. A process according to claim 1 or claim 2 wherein said aliphatic hydrocarbon is about 4 to 6 weight % of the total feed.

14. A process according to claim 1 or claim 2 wherein said aliphatic hydrocarbon is n-pentane and further including introducing into said isomerization zone from about 1–10 weight percent of the total feed to the isomerization zone, of toluene.

* * * * *